United States Patent
Carrión et al.

(10) Patent No.: US 6,630,299 B2
(45) Date of Patent: Oct. 7, 2003

(54) FLUORESCENCE DETECTION

(75) Inventors: Miguel E. Carrión, New Market, MD (US); Marilyn Menger, Derwood, MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

(21) Appl. No.: 09/888,681

(22) Filed: Jun. 25, 2001

(65) Prior Publication Data

US 2002/0045160 A1 Apr. 18, 2002

Related U.S. Application Data

(62) Division of application No. 09/679,439, filed on Oct. 4, 2000, now Pat. No. 6,447,995.

(51) Int. Cl.[7] .............................. C12Q 1/00; C12Q 1/02; C12Q 1/06; C12N 15/861; A61K 39/235

(52) U.S. Cl. .............................. 435/5; 435/8; 435/320.1; 435/173.1; 435/173.9; 424/233.1

(58) Field of Search .............................. 435/5, 8, 320.1, 435/173.1, 173.9; 424/233.1

(56) References Cited

U.S. PATENT DOCUMENTS

| | | |
|---|---|---|
| 3,887,812 A | 6/1975 | Hirschfeld |
| 4,222,743 A | 9/1980 | Wang |
| 4,979,824 A | 12/1990 | Mathies et al. |
| 5,221,958 A | 6/1993 | Bohnenkamp |
| 5,323,008 A | 6/1994 | Studholme et al. |
| 5,604,096 A | 2/1997 | Schaeffer et al. |
| 5,623,932 A | 4/1997 | Ramanujam et al. |
| 5,631,169 A | 5/1997 | Lakowicz et al. |
| 5,665,546 A | 9/1997 | Cubbage et al. |
| 5,733,720 A | 3/1998 | Olivo |
| 5,741,648 A | 4/1998 | Hemstreet, III et al. |
| 5,830,666 A | 11/1998 | Fujita et al. |
| 5,837,520 A | 11/1998 | Shabram et al. |
| 5,895,922 A | 4/1999 | Ho |
| 5,919,445 A | 7/1999 | Chao |
| 5,965,358 A | 10/1999 | Carrión et al. |

FOREIGN PATENT DOCUMENTS

| | | |
|---|---|---|
| CA | 2252972 A | 5/2000 |
| WO | WO 91/09310 A | 6/1991 |
| WO | WO 94/26934 A | 11/1994 |
| WO | WO 96/27677 A | 9/1996 |
| WO | WO 99/43843 A | 9/1999 |
| WO | WO 99/46047 A | 9/1999 |
| WO | WO 99/54348 A | 10/1999 |
| WO | WO 99/54441 A | 10/1999 |
| WO | WO 99/60371 A | 11/1999 |
| WO | WO 00/08182 A | 2/2000 |
| WO | WO 00/08444 A | 2/2000 |
| WO | WO 00/40702 A | 7/2000 |

OTHER PUBLICATIONS

Nalin et al. P.N.A.S. USA, 1990, vol. 87, pp. 7593–7597.*
Lackowicz et al. Flurescence Specroscopy of Biomolecules in Molecular biology and Biotechnology, Edited by Meyers et al. 1995, pp. 317–320.*
Bartlett et al., Nat. Med., 4 (5), 635–637 (May 1998).
Bonneau et al., Anal. Biochem., 255 (1), 59–65 (Jan. 1998).
Castleman et al., Am. J. Vet. Res, 46 (3), 547–553, (Mar. 1985).
Côté et al, Biotechnol. Prog., 13, 709–714 (Nov./Dec. 1997).
Crimmins et al., Biochemistry, 21 (14), 3518–3524 (Jul. 1982).
D'Alessio et al., Appl. Microbiol., 20 (2), 233–239 (Aug. 1970).
Davis et al., Arch. Biochem. Biophys., 346 (1) 125–130 (Oct. 1997).
Fulton et al., J. Virol. Methods, 22, 149–164 (May 1988).
Grimmel et al., Archives of Virology, 78 (3–4), 191–201 (Apr. 1983).
Hara et al., Appl. Environ. Microbiol., 57 (9), 2731–2734 (Sep. 1991).
Haviv et al., J. Neurosci. Res., 50, 69–80 (May 1997).
Hennes et al., Limnol. Oceanogr., 40 (6) 1050–1055 (Jun. 1995).
Hicks, Hum. Pathol., 15, 112–116, (Feb. 1984).
Krüse et al., Eur. J. Biochem., 95, 21–29 (Mar. 1979).
Landry et al., J. Clinical Microbiol., 38 (2) 708–711 (Feb. 2000).
Meyers et al., J. Biol. Chem., 265 (10), 5875–5882 (Apr. 1990).
Miller et al., Ultrastruct. Pathol., 21 (2) 183–193 (Mar./Apr. 1997).
Nakano et al., J. Struct. Biol., 129 (1) 57–68 (Feb. 2000).
Oliveira et al., J. Biol. Chem., 273 (21), 16037–16043 (May 2000).

(List continued on next page.)

Primary Examiner—James Housel
Assistant Examiner—Bao Qun Li
(74) Attorney, Agent, or Firm—Leydig, Voit & Mayer, Ltd.

(57) ABSTRACT

The present invention provides methods of detecting and/or characterizing the viral vector particle content of a medium. A medium is provided and contacted with an excitation energy such that, if a viral vector particle is in the medium, an electron associated with the intrinsically fluorogenic portion of the viral vector particle will be raised to an excited energy state. The excited electron is permitted to emit radiation having an emission wavelength which is detected. The viral vector particle content of the medium then can be evaluated by comparing the detected emission wavelength with a standard signal. For example, the number of viral vector particles in a medium can be quantified by comparing the detected wavelength and its corresponding intensity to a standard signal. Similar methods for evaluating the adenoviral vector particle content of a medium and the intrinsically fluorogenic adenoviral structural protein content of a medium are provided.

8 Claims, No Drawings

OTHER PUBLICATIONS

Orito et al., *Gut*, 39, 876–880 (Dec. 1996).
Samiotaki et al., *Anal. Biochem.*, 253, 156–161 (Nov. 1997).
Taliani et al, *Anal. Biochem.*, 240 (1) 60–67 (Aug. 1996).
Tanaka et al., *J. Hepatol.*, 23, 742–745 (Jul. 1995).
Trabelsi et al., *Eur. J. Clin. Microbiol. Infect. Dis.*, 11 (6), 535–539 (Jun. 1992).
Volkin et al., *J. Pharm. Sci.*, 86 (6), 666–673 (Jun. 1997).
Wood et al., *J. Medical Virol.*, 51, 198–201 (Sep. 1996).
Wu et al., *Biochemistry*, 36, 6115–6123 (Feb. 1997).
Yoon et al., *Anal. Biochem.*, 277 (2) 228–231 (Jan. 2000).
Zaharia et al, *Rev. Roum. Med.—Virol.*, 32 (1) 29–39 (Jan./Feb./Mar. 1981).

* cited by examiner

FLUORESCENCE DETECTION

This is a divisional of application Ser. No. 09/679,439, filled on Oct. 4, 2000, which is incorporate by reference.

TECHNICAL FIELD OF THE INVENTION

This invention pertains to the detection and characterization of viral vector particles, particularly through the use of fluorescence.

BACKGROUND OF THE INVENTION

Viral vectors are of significant importance in several aspects of molecular biology and medicine. Numerous types of viral vectors have been developed for use as gene delivery vehicles. Examples of such viral vectors include vectors based on adenovirus (Ad), adeno-associated virus (AAV), baculovirus, herpes simplex virus (HSV), and murine leukemia virus (MLV). Compared to other methods of delivering genetic information (e.g., lipo some-associated delivery techniques or naked DNA vectors), viral vectors offer several advantages, including higher rates of delivery and better targeting of specific tissues and/or cells. With the increased use of viral vectors for therapeutic, as well as diagnostic, applications there is an increasing need for better methods for quantification and characterization of viral vector particles.

Several techniques are known for the characterization and/or quantification of viral vector particles, including chromatographic methods and mass spectrometry (see, e.g., International Patent Application WO 99/54441, International Patent Application WO 00/40702, and U.S. Pat. No. 5,965,358). Presently, the quantification of viral vector particles is most commonly carried out by the use of ultraviolet (UV) radiation. For example, U.S. Pat. No. 5,837,520 discloses monitoring the absorbance of a chromatographic eluant of viral particles at a selected UV wavelength and comparing the absorbance value to a standard curve which relates absorbance to the number of viral vector particles. Ultraviolet absorbance is limited in its sensitivity and requires a large number of viral particles (typically about $5 \times 10^9$ particles/ml) for accurate detection (where the standard deviation in measurement is about 10% or less). Due to the large number of viral particles required for accurate quantification, ultraviolet absorbance is not useful in applications requiring small populations of viral particles, such as viral vector-based gene therapies where high quantities of viral vector particles can be undesirable.

Fluorescence-based detection and quantification of viral particles associated with fluorogenic dyes such as fluorescein isothiocynate (FITC) is known in the art. For example, Hara et al., *Applied and Environmental Microbiology*, 57(9), 2731–34 (1991), describes the use of epifluorescent microscopy on DAPI (4',6'-diamidino-2-phenylindole)-treated water samples to determine numbers of bacteria, viruses, and DNA-associated particles. More recently, Hennes and Suttle, *Limnol. Oceanogr.*, 10(6), 1050–55 (1995), describes similar research using the cyanine-based dye, Yo-Pro-1.

Immunofluorescence, which combines antibody-antigen binding and fluorophore-associated fluorescence detection (see, e.g., Tanaka et al., *J. Hepatology*, 23, 742–45 (1995)), also has been used to detect and/or characterize viruses. For example, D'alessio et al., *Applied Microbiology*, 20(2), 233–39 (1970), discloses the use of fluorescein-based immunofluorescence techniques to detect influenza viruses, herpes simplex virus, and adenoviruses. More recently, Orito et al., *Gut*, 39, 876–880 (1996), described the use of a fluorescent enzyme immunoassay (FEIA) to quantify hepatitis C virus core protein levels in patients, and Wood et al., *J. Medical Virol.*, 51, 198–201 (1997), describes the use of FITC-based immunofluorescence to identify and type adenovirus isolates. Enzymatic techniques associated with fluorogenic dyes also are capable of detecting nucleic acids (see, e.g., U.S. Pat. No. 5,830,666).

The Green Fluorescent Protein (GFP), obtained from the jellyfish *Aequorea victoria* (see, e.g., Prasher et al., *Gene*, 111, 229–33 (1992)), which is intrinsically fluorogenic, has been used to characterize viruses by causing viruses to express GFP. For example, International Patent Application WO 00/08182 describes preparations of herpes virus expressing GFP fusion proteins to detect the progress of cell infection by the virus and to screen for neutralizing antibodies or inhibitors of infection. International Patent Application WO 99/54348 discloses the use of vectors transfected with short-lived GFP variants to assay activation or deactivation of promoters. International Patent Application WO 99/43843 teaches transfection with adenovirus vectors encoding GFP and tracking viral production by GFP-associated fluorescence.

Techniques for detecting or characterizing viral vector particles based on direct fluorescent dye-association with the viral particles, immunofluorescence, and GFP-associated viral fluorescence are limited in requiring either a fluorogenic dye or GFP to be associated with the viral vector particles. Because the use of fluorogenic dyes can be expensive, less sensitive than other techniques, and damaging to samples, direct dye-association techniques are often unsuitable. Immunofluorescence, while more sensitive than direct dye-based techniques, requires specific epitopes and antibodies. GFP-based techniques require either chemical or genetic modification to associate the viral vector particles with GFP.

Few fluorogenic methods have been used to study biological materials without the use of dyes or strong fluorogenic proteins such as GFP. U.S. Pat. No. 5,623,932 discloses the use of direct fluorogenic methods to differentiate between normal and abnormal cervical tissues. The '932 patent discloses using laser-induced fluorescence (LIF) to identify fluorogenic spectra associated with healthy tissue, relying on oxy-hemoglobin and NADH in the tissue as fluorophores, and further using such spectra to identify "abnormal" tissues by comparing spectra. The '932 patent suggests that such abnormal tissue could be inflamed or infected with human papilloma virus (HPV). However, the '932 patent fails to identify, characterize, or quantify HPV particles in such tissues.

Accordingly, there remains a need for techniques which allow for improved detection and characterization of viral vector particles. The present invention provides methods for such detection and characterization through fluorescence detection of viral vector particles and viral vector proteins. These and other advantages of the present invention, as well as additional inventive features, will be apparent from the description of the invention provided herein.

BRIEF SUMMARY OF THE INVENTION

The present invention provides a method of quantifying the number of viral vector particles in a medium. A medium containing a viral vector particle having an intrinsically fluorogenic portion is provided. The medium is contacted with an excitation energy, such that an electron associated with the intrinsically fluorogenic portion of the viral vector particle is raised to an excited energy state. The excited electron is permitted to emit radiation having one or more emission wavelengths and corresponding emission intensities. An emission wavelength, and the intensity of the emitted radiation at the emission wavelength, are detected. The number of viral vector particles in the medium is quantified by evaluating the detected wavelength and intensity and comparing them to a provided standard signal.

The invention also provides a method of evaluating the viral vector particle content of a medium. A medium is provided and contacted with an excitation radiation having an excitation wavelength such that if a viral vector particle is in the medium an intrinsically fluorogenic portion of the viral vector particle will emit radiation having an emission wavelength at about 560–590 nm (e.g., about 575 nm). The viral vector particle content of the medium is evaluated by determining whether the medium emits radiation at about 560–590 nm.

The invention further provides a method of evaluating the adenoviral vector particle content of a medium. A medium is provided and contacted with an excitation radiation having one or more excitation wavelengths suitable for exciting an electron associated with the intrinsically fluorogenic portion of an adenoviral vector (typically at about 235 nm, about 284 nm, or both). If an adenoviral vector particle is in the medium, an intrinsically fluorogenic portion of the adenoviral vector particle will emit radiation having an emission wavelength characteristic of a naturally-occurring (i.e., wild-type) adenoviral vector (typically at about 330 nm, about 574 nm, or both). The adenoviral vector particle content of the medium is evaluated by determining whether the medium emits radiation having such an emission wavelength (or wavelengths).

The invention also provides a method of evaluating the intrinsically fluorogenic adenoviral structural protein content of a medium. Similar to the other aspects of the invention, a medium is provided and contacted with an excitation radiation having an excitation wavelength, such that if an intrinsically fluorogenic adenoviral structural protein is in the medium it will emit radiation having an emission wavelength characteristic of an intrinsically fluorogenic wild-type adenoviral structural protein or a substantial homolog thereof. The intrinsically fluorogenic adenoviral structural protein content of the medium is evaluated by determining whether radiation having an emission wavelength characteristic of an intrinsically fluorogenic wild-type adenoviral structural protein or substantially homologous protein is emitted from the medium.

DETAILED DESCRIPTION OF THE INVENTION

The present invention provides methods of detecting and/or characterizing (e.g., quantifying) the viral vector particle content of a medium. A medium in the context of the present invention is any medium which is suitable for detection of radiation emitted from a wild-type intrinsically fluorogenic portion (or portions) of a viral vector, or substantial homolog thereof, using the disclosed inventive methods. The medium can include different types of intrinsically fluorogenic viral vector particles, other fluorogenic molecules and non-fluorogenic molecules. The medium can take any suitable form. Typically, the medium will include or be in the form of a liquid, such as an aqueous solution. Such solutions can consist of numerous additional components, such as buffers, stabilizers, preservatives, excipients, carriers, diluents, or other additives. The medium can comprise a pharmaceutically acceptable (e.g., a physiologically acceptable) carrier and can take the form of a pharmaceutical composition. The medium can include one or more cells. For example, the medium can be a culture of cells, or a tissue, which is either in a tissue culture or in an animal (e.g., an organ in a human). The medium can consist of a sample of a larger composition, such as a pool or stock of viral vector particles (e.g., a library of viral gene transfer vector particles in a stock).

The medium can, and typically will, contain a viral vector particle having an intrinsically fluorogenic portion. The invention can be practiced with any suitable type of viral vector particle. A viral vector particle is any molecule which is based upon, derived from, or originates from a virus, and which includes more than one type of viral molecule (e.g., more than one type of viral protein or a viral protein and a viral nucleic acid) or a substantial homolog thereof (as defined further herein). A viral molecule is any molecule which makes up a portion of a wild-type virus or a substantial homolog thereof.

The viral vector particle can be an unmodified naturally occurring (i.e., "wild-type") virus particle, or modified viral vector particle, such as a viral gene transfer vector and/or a synthetic viral vector particle. Desirably, the viral vector particle contains, or is associated with, a nucleotide genome. Preferably, though not necessarily, the viral vector particle is derived from, is based on, comprises, or consists of, a virus which normally infects animals, such as mammals and, especially, humans. Preferred types of viral vector particles include baculovirus vectors, herpes vectors, retroviral vectors, adeno-associated viral vectors, and adenoviral vectors. Adenoviral vector particles are particularly preferred.

The inventive method can be practiced with a medium containing any suitable number of viral vector particles. A suitable number of viral vector particles is any number which can be detected and/or characterized (e.g., quantified) by the methods of the present invention. The inventive methods can be practiced with a homogenous or heterogeneous (i.e., mixed) population of viral vector particles (e.g., wild-type herpes virus and adenovirus particles, or different modified particles such as replication defective adenoviral vector particles and complementing (i.e., helper) adenovirus particles). When a number of identical or similar viral vector particles are present in a suitable medium, the particle-containing medium can be referred to as a stock of the viral vector.

The viral vector particle can have any suitable size and weight. In contrast to UV spectrophotometry-based techniques, viral vector particles with relatively larger molecular weights and sizes can be detected, characterized, and/or quantified directly using the methods described herein, without performing calculations or taking additional steps to account for scattered light problems associated with UV-based detection which may result in erroneous detection readings. For example, viral vector particles having molecular weights of about $1 \times 10^8$ Daltons or more, about $1.5 \times 10^8$ Daltons or more, and even about $1.7 \times 10^8$ Daltons or more (e.g., about $2 \times 10^8$ Daltons or more) can be detected and/or characterized (e.g., quantified) directly (i.e., without taking additional steps or performing calculations to account for light scattering). Further in contrast to UV spectrophotometry-based techniques, viral vector particles with large particle sizes can be directly detected and/or characterized (e.g., quantified). For example, viral vector particles of at least about 40 nm in diameter, at least about 80 nm in diameter, at least about 120 nm in diameter, or larger, can be directly detected and/or characterized.

The viral vector particle includes an intrinsically fluorogenic portion. The intrinsically fluorogenic portion in the context of the present invention is any portion of a viral vector particle which includes, or consists of, a naturally-occurring (wild-type) viral molecule (e.g., an intrinsically fluorogenic viral protein), or a substantially homologous (preferably substantially identical) molecule, which is intrinsically fluorogenic. A molecule is "intrinsically fluorogenic" if it emits one or more emission wavelengths when contacted with a suitable excitation energy in the absence of fluorescent dyes and/or conjugated fluorophores.

Typically, and preferably, the intrinsically fluorogenic portion includes, or consists of, a wild-type viral molecule. In such aspects, the molecule can be any suitable type of molecule. Examples of suitable molecules include viral proteins, including post-translationally modified viral proteins (e.g., viral glycoproteins).

The intrinsically fluorogenic portion can include, or consist of, an intrinsically fluorogenic molecule that is at least substantially homologous, preferably substantially identical, to an intrinsically fluorogenic wild-type viral molecule (e.g., a non-wild-type homolog of a wild-type viral fluorogenic protein). As used herein, a substantially homologous molecule is any molecule having at least about 70% amino acid sequence homology to another molecule (e.g., a wild-type viral protein), at least about 70% structural similarity to another molecule (e.g., a wild-type viral protein), or both.

The intrinsically fluorogenic portion has at least about 70% (e.g., at least about 80%, at least about 85%, or at least about 90%) amino acid sequence homology to an intrinsically fluorogenic wild-type viral molecule if at least about 70% of the amino acid residues in the substantially homologous molecule's amino acid sequence are identical to, or differ by only conservative amino acid residue substitutions from, the amino acid residues in the amino acid sequence of its wild-type counterpart when the sequences are compared in a manner which maximizes homology and/or identity. Conservative amino acid residue substitutions involve exchanging a member within one class of amino acid residues for a residue that belongs to the same class. Homologous proteins obtained by conservative substitutions are expected to substantially retain the biological properties and function of the wild-type protein. The classes of amino acids and the members of those classes are presented in Table 1.

TABLE 1

Amino Acid Residue Classes

| Amino Acid Class | Amino Acid Residues |
| --- | --- |
| Acidic Residues | ASP and GLU |
| Basic Residues | LYS, ARG, and HIS |
| Hydrophilic Uncharged Residues | SER, THR, ASN, and GLN |
| Aliphatic Uncharged Residues | GLY, ALA, VAL, LEU, and ILE |
| Non-polar Uncharged Residues | CYS, MET, and PRO |
| Aromatic Residues | PHE, TYR, and TRP |

A substantially homologous molecule can include any suitable number of non-conservative amino acid residue substitutions. Preferably, aromatic residues (which are fluorogenic) remain conserved with respect to, and more preferably remain identical to, the aromatic residues occurring in the corresponding wild-type viral molecule.

One of ordinary skill will recognize that residue position in either substantially homologous or substantially identical molecules may vary from their wild-type counterpart molecule due to deletions or additions of residues. Homology and/or identity in view of such substitutions and deletions can be determined using commercially available sequence analysis/alignment software and/or other known techniques. Protean, sold by DNASTAR (Madison, Wis.), is an example of suitable commercially-available sequence analysis software.

Alternatively or additionally, the intrinsically fluorogenic portion has at least about 70% (e.g., at least about 80%, at least about 85%, or at least about 90%) structural similarity to an intrinsically fluorogenic wild-type viral molecule. Thus, the intrinsically fluorogenic portion can have a significantly different amino acid sequence from wild-type viral proteins if there exists such structural similarity. For example, the invention can be practiced with synthetic peptides and/or recombinantly produced peptides that have a structure that is substantially similar to the structure of wild-type adenovirus fiber protein. Examples of such proteins include modified fiber proteins that contain knob (or "head") region or domain modifications as described in, e.g., U.S. Pat. No. 5,846,782, and double-ablated adenoviruses that contain modified penton proteins.

The percentage of structural similarity can be based on complete overlap between the molecules, on a domain-by-domain basis, or, preferably, by both methods. Structural similarity between the molecules can be determined by any suitable method. For example, the secondary structure of two proteins can be determined and compared, e.g., by means of performing surface probability comparisons using the amino acid sequences of both molecules. Alternatively, and preferably, the three dimensional structures for the two proteins are determined and compared (e.g., by overlapping the three dimensional structures of the proteins using three dimensional imaging software).

The intrinsically fluorogenic portion can be substantially identical to an intrinsically fluorogenic wild-type viral molecule such that it has at least about 70% (preferably at least about 80%, and more preferably at least about 90%) amino acid sequence identity with a wild-type viral protein. Preferably, although not necessarily, the intrinsically fluorogenic portion also will have at least 70% structural similarity to its wild-type viral counterpart.

The intrinsically fluorogenic portion desirably has at least similar fluorogenic properties to its wild-type viral counterpart. In other words, the intrinsically fluorogenic portion preferably emits radiation having at least one emission wavelength in common with its wild-type viral counterpart.

The viral vector particle can include, and preferably does include, more than one intrinsically fluorogenic portion, and each intrinsically fluorogenic portion preferably includes more than one intrinsically fluorogenic molecule (e.g., 3, 5, 10, 15, or more intrinsically fluorogenic wild-type viral proteins). Additionally or alternatively, the viral vector particle can include non-natural and/or non-viral fluorogenic portions in addition to the intrinsically fluorogenic portion (e.g., the viral vector particle can include GFP).

The intrinsically fluorogenic portion can make up any suitable portion of the viral vector particle, including the entire particle. Desirably, the molecules which make up the intrinsically fluorogenic portion (or portions) make up at least about 10%, preferably at least about 20%, more preferably at least about 50%, and even more preferably at least about 70% of the molecules which form the viral vector (either by weight, molecule type, or both).

The viral vector particle-containing medium is contacted with an excitation energy. The excitation energy can be any form of energy which is capable of exciting an electron associated with an intrinsically fluorogenic portion of the viral vector particles to an excited energy state. While numerous forms of energy are suitable, the excitation energy preferably is in the form of an excitation radiation.

Excitation radiation can be any suitable type of radiation. Typically, the excitation radiation will be in the form of electromagnetic radiation having one or more discrete wavelengths. For example, the excitation radiation can be in the form of visible light radiation, such as is emitted from a suitable lamp. Alternatively, the excitation radiation can be in the form of ultraviolet radiation (UV) or infrared (IR) radiation. The excitation radiation can be generated by any suitable technique or device. Most often, the excitation radiation is in the form of one or more photons of energy supplied by a suitable radiation source, such as an incandescent lamp, argon/mercury lamp, xenon lamp, halogen lamp, or a laser (e.g., through a laser-induced flash).

Due to the speed with which excitation occurs using a xenon lamp or a laser, the excitation energy is preferably provided by one of these two sources. Because of its high sensitivity, laser-induced fluorescence (LIF) is particularly preferred. In LIF, the medium typically is irradiated at one wavelength, usually in the UV spectral region, and the emission (fluorescent signal) is measured at a longer wavelength, usually at a higher UV wavelength or the violet-yellow/green region of the visible spectrum. The excitation source for molecular LIF typically is a tunable dye laser in the UV spectral region. In addition to UV radiation, LIF can utilize visible and/or near-IR excitation radiation, particularly with recently developed frequency doubling methods. Cooling of the medium (and thus the viral vector particle), for example by molecular beams, free-jet expansions, and cryogenic glass or crystalline matrices, in LIF-based techniques, can remove spectral congestion and reduce the Doppler width of the transitions, thereby allowing for improved detection. The laser used for LIF can be any suitable laser, including, for example, an argon-ion laser or a helium/neon laser. Preferred laser fluorometers are ZetaLIF fluorometers, available from Picometrics (Ramonville, Saint Agne, France). Typically, in using LIF techniques, the medium will be, or comprise, a sample (i.e., a portion) of a larger composition due to the tendency of LIF techniques to damage biological samples, including viable viral vector particles. Due to the higher sensitivity associated with LIF-based techniques, such samples can be relatively small and consist of very few viral vector particles (e.g., samples containing about $1 \times 10^6$ viral vector particles or less are suitable), and the results of applying the method can be extrapolated to quantify or otherwise characterize or evaluate the viral vector particles in a significantly larger composition.

An electron associated with an intrinsically fluorogenic portion of the viral vector particle is raised to an excited energy state by the contact of the excitation energy with the medium. The process of raising the electron to an excited energy state is known as excitation, and the electron in such a state is referred to as an excited electron. Excitation in the context of the present inventive method can occur in any suitable manner. For example, excitation can occur through direct contact of the viral vector particle with the excitation energy, or, alternatively, through absorption of the excitation energy and transfer thereof through the medium to the viral vector particle. Any suitable number of electrons can be raised to the excited state by the excitation energy. Desirably, more than one electron is excited. Thus, each viral vector particle desirably includes an intrinsically fluorogenic portion associated with more than one excited electron.

The excited energy state can be any suitable energy state which is higher than the energy state which the electron occupied immediately prior to contact with the excitation energy. A suitable energy state is any energy state which causes the excited electron, if permitted, to emit radiation. Thus, the excited electron can be raised (i.e., "boosted") to the next highest energy state it can occupy (a first excited state (e.g., an $S_1$ state)), or to a higher energy state which the electron can occupy (a second or higher excited state (e.g., an $S_2$ state)). An electron's energy state can be characterized based on the vibrational energy, the rotational energy, or both, associated with the energy state. Several vibrational and rotational energy levels can exist within an excited state.

A radiation wavelength associated with exciting an electron is an excitation wavelength. The excitation wavelength associated with a particular viral vector particle is dependent upon the fluorogenic properties of the particular viral vector. The radiation wavelength associated with exciting the largest number of viral vector particles is the optimum excitation wavelength. The optimum excitation wavelength can be determined by determining the excitation wavelength associated with the apex of the highest "peak" on a graph of the viral vector particle's excitation spectrum (i.e., a two-dimensional plot of either excitation energies or wavelengths versus the intensity of the resulting emitted radiation).

The viral vector particle can have any suitable number of associated excitation wavelengths. Preferably, the viral vector particle has more than one associated excitation wavelength. In such situations, quantification of the number of viral vector particles typically is practiced using the optimum excitation wavelength, which provides the greatest sensitivity and most accurate detection of viral vector particles. In some situations, however, using other excitation wavelengths is preferred. For example, an excitation energy associated with the viral vector particles, which does not excite other (i.e., non-viral vector) fluorogenic components of the medium, can be used to provide greater selectivity for the viral vector particles, even if the excitation radiation is not the optimum excitation wavelength.

Excitation of other fluorogenic components of the medium also can be avoided by the use of wavelength selectors, which are known in the art. A wavelength selector screens radiation, thereby permitting only certain wavelengths, or bands (i.e., ranges) of wavelengths, to contact the medium. Any suitable type of wavelength selector can be used. Typical wavelength selectors include monochromators, bandpass filters (such as long pass and short pass filters), and cutoff filters. A monochromator or a bandpass filter permits a range of wavelengths of an excitation radiation to pass through and contact the medium while blocking radiation at the other excitation wavelengths. A monochromator increases the intensity of the resulting fluorescent emissions by selecting for a range of excitation wavelengths. A cutoff filter blocks stray excitation radiation below a predefined cutoff point. Monochromators, bandpass filters, and other components can be included within a fluorescence detection system. For example, the system can include one or more gratings which are designed to optimize excitation and/or emission wavelengths, alone or in combination with one or more mirrors for directing excitation radiation to the medium or a portion thereof.

After excitation, the excited electron, if permitted to, will emit radiation having one or more emission wavelengths. This phenomenon of emitting radiation by an excited electron concomitant with the excited electron's return to a ground or relaxed state is known as fluorescence. The excited electron's emission of radiation (also known as a fluorescent emission) permits the excited electron to enter an energy state lower than the excited energy state (sometimes referred to as the ground or relaxed state), which typically is substantially equal to the energy state the electron was in prior to contact with the excitation energy.

Fluorescent emissions are marked by brief excitation emission periods. Fluorescent emissions usually begin almost instantaneously upon absorption of radiation at a suitable excitation wavelength. After excitation, fluorescent emissions can occur for any suitable period. Preferably, fluorescent emissions occur for about $5 \times 10^{-3}$ seconds or less. Typically, fluorescent emissions will occur within a period of about $1 \times 10^{-5}$–$1 \times 10^{-9}$ seconds.

The emitted radiation can have any suitable number of emission wavelengths. The magnitude of the emission wavelengths is dependent upon the excitation wavelength and fluorogenic characteristics of the viral vector particle, particularly the energy levels available to the viral vector particle-associated excited electrons. Similar to excitation wavelengths, emission wavelengths can form an emission spectrum, which can be graphically represented as a plot of emission wavelengths versus fluorescence intensity.

Because of energy dissipation during absorption, the emission wavelength or wavelengths typically are longer than the excitation wavelength or wavelengths. The difference in energy or wavelength represented by the difference between the excitation wavelength and the emission wavelength ($h\nu_{EX}$–$h\nu_{EM}$) is known as the Stokes shift. This difference in length of the excitation and emission wavelengths, represented by the Stokes shift, permits isolation of either excitation or emission radiation. Accordingly, viral vector particles associated with large Stokes shifts are preferred.

Fluorescent emissions, in the context of the present invention, can have any suitable characteristics. Preferably, the fluorescent emissions are distinguishable from phosphorescent emissions or luminescent emissions. Thus, for example, the production of fluorescent emissions compared to the use of UV spectrophotometry is relatively temperature independent, except with regard to an increased probability of quenching associated with higher temperatures in some mediums.

The fluorescence process usually is cyclical. Thus, unless the intrinsic fluorogenic capacity of a viral vector particle is irreversibly destroyed in the initial excited state (for example by the phenomenon of photobleaching), a viral vector particle can be repeatedly excited and detected. Thus, the excitation of an electron associated with a viral vector particle can be repeated as desired depending upon the ability of the viral vector particle to undergo repeated excitation/emission cycles.

Often, not all of the electrons initially excited return to the lower energy state by fluorescence. Other processes such as collisional quenching, fluorescence energy transfer, and intersystem crossing also can depopulate the population of excited electrons. The ratio of the number of fluorescence emissions to the number of photons absorbed by a viral vector particle is the fluorescence quantum yield. Thus, the quantum yield measures the relative extent to which processes which depopulate the population of excited electrons occur.

In order to maximize the quantum yield, the methods of the present invention preferably are practiced while avoiding photobleaching (i.e., photodestruction) and quenching of the fluorogenic properties of the viral vector particle. Any suitable technique for avoiding photobleaching and quenching can be utilized. Examples of suitable techniques include avoiding high intensity excitation radiation, maximizing detection sensitivity (e.g., by using low-light detection devices such as CCD cameras, as well as high-numerical aperture objectives, and the widest emission bandpass filters compatible with satisfactory signal isolation), using antifade agents, and avoiding agents associated with collisional quenching, such as $O_2$ and heavy atoms such as iodide. When the medium is in solution (e.g., a portion of a composition subjected to a chromatography resin), degassing the composition to remove such agents, particularly oxygen, and thereby avoid collisional quenching, is particularly preferred. In live cell-containing mediums, vitamin C (ascorbic acid) often can be used to reduce photobleaching. Collisional and self-quenching also can often be reduced, if necessary, by reducing the concentration of the viral vector particles and/or other components in the medium. Quenching is conformation dependent. Thus, modifying the conformation of the viral vector particles also can affect the probability of quenching. Environmental factors, such as medium polarity, proximity and concentrations of quenching species, and pH, also should be monitored for photobleaching effects.

The emitted radiation can be characterized on the basis of its intensity (also sometimes referred to in the art as brightness). The total intensity of viral vector particle emitted radiation in a particular medium is a function of the intensity and wavelength of the excitation radiation, the amount of viral vector particles present in the medium, and the fluorogenic properties of the viral vector particles.

Two fluorogenic properties of the viral vector particles which affect intensity are the extinction coefficient and quantum efficiency. The extinction coefficient is the amount of radiation of a given wavelength that is absorbed by the viral vector particle upon contact with the excitation radiation. The quantum efficiency of the viral vector particle is its capacity to convert such absorbed radiation to emitted fluorescent radiation. The molar extinction coefficient of a viral vector particle is defined as the optical density of a one-molar solution of viral vector particles through a one-cm radiation path. Emission intensity is proportional to both the quantum efficiency and extinction coefficient.

The emitted radiation, particularly the wavelength and intensity of the emitted radiation corresponding to at least one emission wavelength, is detected. If the viral vector particle emits radiation at multiple emission wavelengths, it is typically preferred that the method includes determining the intensity of emitted radiation at those wavelengths as well. Any suitable number of emission wavelengths, and intensities corresponding to any number of emission wavelengths, can be detected.

The emitted radiation can be detected using any suitable technique. Preferably, a fluorescence detector is used to detect the emitted radiation. Any suitable fluorescence detector can be used, and numerous types are known and commercially available. Generally, a fluorescence detector registers emission radiation, including emission wavelengths, intensities, or both, and produces a recordable output, usually as an electrical signal or a photographic image. To aid detection, the fluorescence typically interacts with an emission wavelength selector (such as a monochromator or an interference filter) and then is detected by a radiation detector, such as a photodiode or a photomultiplier tube (PMT). Other radiation detectors, such as a CCD camera, also can be used.

Suitable fluorescence detectors include fluorometers (sometimes referred to in the art as fluorimeters), spectrofluorometers, and microplate readers, which measure the average fluorescent properties of the medium; fluorescence microscopes, which resolve fluorescence as a function of spatial coordinates in two or three dimensions; fluorescence scanners, which resolve fluorescence as a function of spatial coordinates in two dimensions for macroscopic objects such as electrophoresis gels, blots, and chromatograms; and flow cytometers, which measure fluorescence per particle in a flowing stream, allowing subpopulations of viral vector particles in the medium to be identified, evaluated, and quantified. Each type of instrument produces different measurement artifacts and makes different demands on the viral vector particles. For example, although photobleaching is often a significant problem in fluorescence microscopy, it is not a major impediment in flow cytometry because the dwell time (how long the excitation beam continues to illuminate the medium) of the individual viral vector particles cells in the excitation beam in flow cytometry is short. PMTs can be useful in low intensity applications such as fluorescence spectroscopy and are often integrated into such devices; however, other radiation detectors also are suitable.

Preferably, the fluorescence detector provides continuous ranges of excitation and emission wavelengths, in contrast to laser scanning microscopes and flow cytometers, which presently typically require excitation at a single fixed wavelength. Fluorometers and/or spectrofluorometers, which provide such qualities, are preferred fluorescence detectors. Generally, a fluorometer is a fluorescence detector which includes an excitation source, a sample cell for testing the medium (which typically is a portion of a larger composition), and a radiation detector, such as a PMT.

As indicated above, scanning fluorescence techniques are useful in many aspects of the invention. Examples of such techniques include moving a laser over the medium or, alternatively, using a CCD camera to collect the entire image at once. CCD camera techniques are faster and potentially more sensitive than scanning, but often provide lower resolution than PMT-based scanning techniques. Other detection configurations have been developed using multiple lasers, rotating mirrors, and mounts that fix the laser and detectors in a constant position, each of which provides different and particular advantages. For example, certain configurations can permit the determination of the shape and/or weight of the viral vector particle (e.g., systems which use a fluorometer similarly to a light scatter detector).

Detecting fluorescent emissions sometimes can be compromised by background signals, which may originate from other medium constituents (sometimes referred to in the art as autofluorescence). Autofluorescence desirably is minimized. Autofluorescence can be minimized by using a suitable wavelength selector, such as a filter that reduces the transmission of background signals (e.g., a bandpass filter). Alternatively, in three-dimensional imaging systems, confocal optics improve resolution in the third dimension. Such systems irradiate sequentially each point in three-dimensional space. Collection optics collect the signal from the irradiated point and reject any information that is out of focus. If the viral vector particles are associated with multiple excitation wavelengths, the use of longer wavelengths also can assist in avoiding background fluorescence. Another way to improve the signal is to increase the viral vector particle concentration; however, in most instances care should be taken to avoid quenching caused at very high viral vector particle density.

There are numerous other ways to improve signal detection and evaluation. For example, the excitation radiation can be eliminated from the collection pathway by several methods, including orienting the path of the excitation radiation so that the excitation radiation avoids contacting the detection pathway and inserting bandpass filters into the detection pathway to reject the excitation wavelength. Fluorescent signal strength also can be improved by increasing the dwell time or repetitively scanning the sample and mathematically processing the signals to reduce random noise.

A standard signal can be provided, and the number of viral vector particles in the medium can be quantified, by comparing the intensity of the detected fluorescent emissions emanating from the viral vector particle or particles with the standard signal. The intensity of the radiation emanating from the viral vector particle or particles is typically proportional to the number of viral vector particles emitting radiation, thereby permitting relative quantification of the viral vector particles by comparison to the standard signal. In practice, a radiation detector (such as a PMT) which transmits a current proportional to the intensity of the radiation detected by it can be used to determine the intensity.

Quantification can be performed under any suitable conditions. Typically and preferably, wavelength and intensity of the excitation radiation are held constant (for example, using a controlled laser light source) to ensure proportionality between intensity and the number of viral vector particles. Dwell time also can affect the intensity of the emitted radiation and also should be kept constant when determining intensity for quantification purposes.

The standard signal can be any suitable signal which permits quantification of the number of viral vector particles in the medium. There are numerous techniques available for obtaining a suitable standard signal. For example, a standard medium having a known viral vector particle content can be used to produce a standard signal (e.g., a standard emission spectrum), which can be compared to the emission spectrum of the medium.

The inventive method can quantify any suitable number of viral vector particles in any suitable concentration. Desirably, the proportionality of the number of viral vectors to emitted radiation intensity is maintained throughout a wide range of viral vector particle concentrations, though this is sometimes not possible at particularly high concentrations. One skilled in the art can determine the suitable quantifiable range of particle concentrations and particle numbers by routine experimentation. For example, the minimum number of viral vector particles for use can be determined by adding viral vector particles to a medium containing no viral vector particles in a stepwise manner, and testing for fluorescence detection after each addition. The maximum concentration and/or particle number can be determined by continuing the steps of stepwise addition of viral vector particles and fluorescence detection until the substantially linear relationship between viral vector particle number and emitted radiation intensity is no longer observed. The fluorescence detector, the type of excitation radiation, and type of viral vector particle, may impact on the range of viral vector particle numbers which can be quantified by the inventive method.

The inventive method can be practiced using mediums containing significantly smaller viral vector particle populations compared to those which can be detected by UV spectrometry. For example, mediums with viral vector concentrations of about $1 \times 10^{10}$ particles/ml or less, about $1 \times 10^9$ particles/ml or less, about $1 \times 10^7$ particles/ml or less, about $5×10^6$ particles/ml or less, about $1×10^5$ particles/ml or less, or even lower concentrations, can be quantified using the inventive method. The amount of viral vector particles required for quantification depends upon the source of the excitation energy. For example, using a xenon lamp to generate the excitation energy permits quantification of about $1×10^7$ particles/ml or less (e.g., about $5×10^6$ particles/ml or less), whereas using LIF to generate the excitation energy permits quantification of about $1×10^5$ particles/ml or less (e.g., about $5×10^6$ particles/ml or less).

While quantification can be performed with any suitable level of accuracy, the present invention offers methods where quantification at such low concentrations is possible with relatively (e.g., compared to UV spectrophotometry) high levels of accuracy. For example, the range of error (or coefficient of variation) in the detected quantity of viral vector particles using the techniques described herein is typically about 15% or less, preferably about 10% or less, even more preferably about 5% or less, and optimally about 3% or less.

In some instances, fluorescence detection by UV spectrometry-based techniques can be desirable. For example, when the methods described herein are used to detect viral vector particles by fluorescence detection and the medium contains a very large population of viral vector particles (e.g., about $1-2×10^{10}$ particles or more), UV spectrometry-based quantification of viral vector particles may be desirable.

As indicated above, the inventive method can be practiced using mediums consisting of a crude cell lysate of viral vector infected cells or with purified lysates. Purification can significantly improve the accuracy of quantification and remove improperly processed (i.e., empty or defective) or otherwise damaged viral vector particles. Any suitable technique for purification can be used. Examples of suitable purification techniques include chromatographic purification (e.g., anion exchange chromatography purification), filtration purification (e.g., tangential flow ultrafiltration), and density gradient purification (e.g., cesium chloride (CsCl) density gradient purification). Such techniques can be combined or repeated as desired.

Purification by chromatography is preferred. Any suitable type of chromatographic purification can be used. Preferably, chromatography purification is performed using the anion exchange chromatography methods described in International Patent Application WO 99/54441. Desirably, the medium is provided by contacting chromatography resin with a composition comprising a viral vector particle, and eluting at least a portion of the composition containing the viral vector particle from the chromatography resin, such that the time of elution of the viral vector particle from the chromatography resin is determinable. The time of elution of the viral vector particle provides another tool for evaluating the viral vector particle content of the medium. Particularly, by separating a viral vector particle containing composition on the basis of elution from a chromatography resin and applying the inventive method to one or more of the portions of the separated composition (i.e., treating each portion as a separate medium for purposes of the inventive method), one can distinguish between the viral vector particle and other fluorogenic components of the medium exhibiting similar emission wavelengths on the basis of their respective elution times. Moreover, when the expected time of elution of the viral vector particle is known, such techniques provide a way to ensure that a detected fluorescent emission is associated with the viral vector particle, by comparing the observed time of elution with a standard (e.g., expected) time of elution. In addition, graphing elution time against fluorescence intensity provides an elution spectrum. Such elution spectrums can be used for relative quantification purposes. Fluorescence detection can be performed directly on the portion(s) of the composition suspected of containing the viral vector particle as such portion(s) elute from the chromatography resin.

Purified mediums, when used, can be purified to any suitable level. Preferably, a purified medium is at least as pure as a lysate of viral vector infected cells subjected to 1×CsCl density gradient purification. More preferably, the medium is at least as pure as a lysate subjected to 2×(i.e., twice repeated) CsCl density gradient purification, and even more preferably is substantially as pure as a 3×CsCl density gradient purified lysate. Examples of techniques for achieving high levels of purification are described, for example, in International Patent Application WO 99/54441.

The present invention also provides a method of quantifying the number of damaged viral vector particles, such as the number of defective viral vector particles, empty viral vector particles, or both, in the medium, by fluorescence detection. Defective viral vector particles are viral vector particles which are incompletely processed (i.e., contain one or more incompletely processed components such that they are not as intact as a fully processed viral vector particle). Empty viral vector particles are particles which do not contain substantially any (e.g., about 10% or less, more typically about 5% or less, and even more typically about 1% or less) of their typical nucleic acid content.

Quantification of defective viral vector particles, empty viral vector particles, otherwise damaged particles, or any combination thereof can be performed with any type of viral vector particle that exhibits different emission spectrums when such particle is empty, defective, or otherwise damaged as compared to a fully intact viral vector particle, i.e., a fully processed viral vector that is not empty, defective, or otherwise damaged. Typically, such viral vector particles exhibit a change in one or more "damage-sensitive" emission wavelengths, such as a wavelength shift and/or an intensity shift in the radiation emitted from such particles when excited. Thus, by detecting the shift in intensity and/or wavelength the number of defective, empty, or otherwise damaged viral vector particles, or any combination thereof, can be quantified by comparison with a suitable standard signal.

A wavelength shift occurs when a damage-sensitive wavelength corresponding to a fully intact (undamaged) viral vector particle is replaced by a slightly larger or smaller wavelength when the inventive method is practiced with a medium containing a number of defective, empty, or otherwise damaged viral vector particles. A wavelength shift can include any detectable shift in wavelength. Typically, a wavelength shift will be about 20 nm or less (e.g., about 10 nm or less) in magnitude.

The number of defective, empty, or otherwise damaged particles desirably is determined by an intensity shift. An intensity shift occurs when the emitted radiation at a damage-sensitive wavelength has a detectably higher or lower intensity when emitted from defective, empty, or otherwise damaged viral vector particle versus when emitted from a fully intact viral vector particle of the same type of viral vector. Whether a wavelength shift, intensity shift, or both is observed when the medium contains damaged viral vector particles depends on the particular type of viral vector particle.

In quantifying defective viral vector particles, the standard signal can be any suitable standard signal which enables relative determination of the quantity of defective, empty, and/or otherwise damaged particles. For example, the standard signal can correspond to a signal produced from a medium having a relatively known amount of defective, empty, otherwise damaged viral vector particles, or any combination thereof. In that respect, a crude cell lysate of viral vector particles can be enriched as to the number of defective, empty, or otherwise damaged viral vector particles, and a purified stock of viral vector particles which contains relatively few, if any, defective, empty, or otherwise damaged particles, can be can be used to provide standard signals for comparing emission spectrums obtained from other mediums (e.g., a crude cell lysate of viral vector particles). A linear regression between the detected intensities at a damage-sensitive wavelength for the purified stock and the damage particle-enriched lysate allows for the quantification of the number of defective, empty, or otherwise damaged viral vector particles in mediums containing more defective, empty, or otherwise damaged viral vector particles than the purified stock, but less than the damage particle-enriched lysate.

Quantification of the number of defective, empty, or otherwise damaged viral vector particles in a medium can be performed under any suitable conditions. Preferably, such techniques are performed in a medium which is at, and which has been maintained at (e.g., stored at for a period of at least about 1 hour, at least about 12 hours, at least about 24 hours, at least about 1 week, or longer), a substantially constant medium pH, at a substantially constant medium temperature, and free of particle integrity-degrading detergents, to avoid undesired integrity changes, conformation changes, quenching, and/or photobleaching. For example, the inventive method can be performed with a medium including or consisting of a pharmaceutical composition, maintained under the aforementioned medium conditions, which comprises a stock of a viral vector, to assess whether the pharmaceutical composition is suitable for administration (e.g., by examining particle degradation under such conditions). Although particularly desirable in connection with the quantification of the number of defective, empty, or otherwise damaged viral vector particles in a medium, these conditions also can be useful in connection with other aspects of the inventive method concerning the detection and/or characterization (e.g., quantification) of viral vector particles in a medium even in the absence of the quantification of the number of defective, empty, or otherwise damaged viral vector particles in a medium.

Preferably, the viral vector particle also is associated with an emission wavelength that is relatively insensitive to the number of defective, empty, and/or otherwise damaged viral vector particles in the medium. In other words, such a wavelength and/or intensity remains relatively unchanged (e.g., less than about 10%, preferably less than about 5%, and more preferably less than about 3% changed) by the presence of defective, empty, or otherwise damaged viral vector particles in the medium. The total number of viral vector particles and the number of defective, empty, or otherwise damaged viral vector particles then can be relatively quantified by evaluating the emission intensity at the insensitive wavelength and comparing it to a standard signal, doing the same with regard to the emission intensity at the damage-sensitive wavelength or wavelengths, and comparing the two obtained values. The ratio of defective, empty, and/or otherwise damaged viral vector particles to the total number of particles thereby can be determined.

The inventive method described herein can be used to evaluate a protocol for the production of a stock of viral vector particles, such as a stock of a viral gene transfer vector. In such respect, a stock of a viral vector, preferably a viral gene transfer vector, is produced in accordance with a production protocol. The inventive method then is performed on a medium containing the stock, or a portion thereof. The production protocol is evaluated by quantifying the number of viral vector particles in the medium, the number of defective, empty, or otherwise damaged viral vector particles in the medium, or any combination thereof.

Production protocols can be evaluated for any suitable quality and in any suitable manner. For example, different viral vector stock production protocols can be compared for the total number of viral vector particles produced and/or the number of defective, empty, or otherwise damaged particles produced. Using such techniques, one can determine the optimum factors for producing a stock, such as what harvest time is associated with a desired particle yield of total viral vector particles (based on quantity and/or quality of the viral vector particles produced). Another example of a quality which can be evaluated is the consistency of the production protocol.

The inventive method also can be used for evaluating a pharmaceutical composition including a stock of a viral vector, such as a stock of a viral gene transfer vector. The pharmaceutical composition can be any composition containing a stock of a viral vector and a suitable pharmaceutical (e.g., physiological) carrier (such as water, with or without other additives (e.g., sugars, salts, and buffers)). The number of viral vector particles in the pharmaceutical composition can be quantified to determine whether the pharmaceutical composition is suitable for administration. For example, whether the dosage is correct can be evaluated (e.g., whether a desired dose of viral gene transfer vector particles is present). Alternatively or additionally, the number of intact viral vector particles can be determined to assess whether the number and/or percentage of intact viral vector particles in the pharmaceutical composition is acceptable for administration to a patient.

The fluorescence detection methods of the invention can be combined with any number of other fluorescence detection techniques. For example, the viral vector particle can be assessed for its mass or shape. Mass or shape of the viral vector particle can be determined using techniques involving point excitation and/or point collection of emissions, combinations of reflective mirrors, or CCD cameras, which are known in the art. Such methods can provide an additional technique for determination of the quality and/or number of the viral vector particles in the medium.

The invention also provides a method of evaluating the viral vector particle content of a medium. In this respect, a medium, which can be any medium described herein, is provided and contacted with an excitation radiation having an excitation wavelength such that if a viral vector particle is in the medium an intrinsically fluorogenic portion of the viral vector particle will emit radiation having an emission wavelength at about 560–590 nm. The viral vector particle content (e.g., adenoviral vector content) of the medium is then evaluated by determining whether the medium emits radiation at about 560–590 nm.

This method can be used to detect the presence or absence of any viral vector particle (such as an adenoviral vector particle) which includes an intrinsically fluorogenic portion that produces fluorescent emissions having an emission wavelength at about 560–590 nm, more precisely about 570–580 nm, and even more precisely about 574 nm, when contacted with an excitation energy. Any suitable excitation energy described herein can be used. Preferably, the excitation energy maximizes viral vector particle-associated fluorescent emissions at about 574 nm. The method also can be practiced with components of such viral vectors, such as a viral protein or substantial homolog thereof, which has an emission wavelength of about 560–590 nm.

It has been discovered that viral vector particles can be detected by such emission wavelengths which are significantly higher than the emission wavelengths associated with fluorogenic amino acids (e.g., tryptophan) or nucleic acid bases (e.g., uracil). Moreover, detection at such wavelengths offers greater selectivity and possibly greater sensitivity in detection.

As described in connection with other aspects of the present invention, the medium can be provided by contacting a chromatography resin with a viral vector particle-containing composition and eluting the viral vector particle from the chromatography resin. Preferably, if a viral vector particle is in the composition, it will elute at a known (i.e., standard) time. The portion of the composition which would contain a viral vector particle, if present, is used as the medium, thereby verifying that any detected emission wavelengths at about 560–590 nm originate from the viral vector particle rather than some other fluorogenic molecule.

When the medium contains a viral vector particle, the method can further include quantifying the number of viral vector particles, by using the quantification techniques described herein. Thus, for example, the intensity of the emitted radiation associated with the intrinsically fluorogenic portion of the viral vector particle can be determined, and the number of viral vector particles in the medium can be quantified by comparing the intensity of the detected radiation with a standard signal.

The identification and/or quantification of viral vector particles (including the number of defective, empty, or otherwise damaged particles) by fluorescence detection can be verified. For example, the method can further include detecting the mass or shape of any fluorescent molecule in the medium emitting radiation at about 560–590 nm, using techniques described herein or otherwise known in the art.

The invention further provides a method of evaluating the adenoviral vector particle content of a medium through fluorescence detection. It has been discovered that wild-type adenoviral vectors include a capsid which consists essentially of intrinsically fluorogenic proteins. Thus, any adenoviral vector containing a wild-type capsid protein, or a substantial homolog thereof, will include an intrinsically fluorogenic portion. In view of these fluorogenic properties, adenoviral vector particles are particularly well suited for fluorescence detection.

In this respect, a medium, which can be any medium as described herein, is contacted with an excitation radiation such that, if an adenoviral vector particle is in the medium, an intrinsically fluorogenic portion of the adenoviral vector particle will emit radiation having an emission wavelength indicative (i.e., characteristic) of an adenoviral vector particle. The excitation radiation can have any suitable excitation wavelength. Typically, adenoviral vectors are associated with excitation wavelengths of about 220–240 nm, about 270–290 nm, or both; more precisely about 230–240 nm, about 280–290 nm, or both; and even more precisely about 235 nm, about 284 nm, or both.

The adenoviral vector particle content of the medium is evaluated by determining whether radiation having an emission wavelength indicative of the presence or absence of an adenoviral vector particle is emitted upon contacting the medium with the excitation radiation. This determination is arrived at by comparing the detected emission wavelengths with emission wavelengths normally associated with adenoviral vectors. Any suitable wavelength or combination of wavelengths indicative of an adenoviral vector can be used. Typically, adenoviral vector-associated emission wavelengths include wavelengths at about 320–340 nm, about 560–590 nm, or both; more precisely about 328–332 nm, about 570–580 nm, or both; and even more precisely at about 330 nm, about 574 nm, or both.

As described in connection with other aspects of the present invention, the medium can be provided by contacting a chromatography resin with an adenoviral vector-containing composition and eluting the adenoviral vector from chromatography resin. Preferably, if an adenoviral vector particle is in the composition, it will elute at a known (i.e., standard) time. The portion of the composition which would contain an adenoviral vector particle, if present, is used as the medium.

When the medium contains an adenoviral vector particle, the method can further include quantifying the number of adenoviral vector particles, by using the quantification techniques described herein. Thus, for example, the intensity of the emitted radiation associated with the intrinsically fluorogenic portion of the adenoviral vector particle can be determined, and the number of adenoviral vector particles in the medium can be quantified by comparing the intensity of the detected radiation with a standard signal. Preferably, quantification of adenoviral vector particles is performed using an excitation wavelength of about 270–295 nm (e.g., 284 nm) and an emission wavelength of about 560–590 nm (e.g. 574 nm).

The identification and/or quantification of adenoviral vector particles (including the number of damaged particles) by fluorescence detection can be verified. For example, the method can further include detecting the mass or shape of any fluorescent molecule in the medium emitting radiation at wavelengths indicative of adenoviral vector particles, using techniques described herein or otherwise known in the art.

The inventive methods also can include separation and identification of the intrinsically fluorogenic portion of the viral vector particle or components thereof The fluorogenic portion and its components can be separated by any suitable method. For example, the components of a chemically disassociated viral vector particle can be electrophoretically separated, based on size and/or charge. Preferably, separation of the fluorogenic portion or its components is performed by reverse phase chromatography. These separated components can be subjected to fluorescence detection to identify and/or characterize the fluorogenic portion of the viral vector particle.

The invention additionally provides a method of evaluating the intrinsically fluorogenic adenoviral structural protein content of a medium. An intrinsically fluorogenic adenoviral structural protein is any adenoviral protein that is a wild-type adenoviral protein or a substantial homolog, which is intrinsically fluorogenic, and which normally forms a part of, or which can be made a part of, an adenoviral capsid. Such proteins can be obtained, for example, by performing reverse phase chromatography, or other separation methods discussed herein or known in the art, on an adenoviral vector particle. Alternatively, such proteins can be produced by any other suitable technique (e.g., by recombinant DNA technology).

In this respect, a medium is provided, which can be any medium discussed herein, and contacted with an excitation radiation having an excitation wavelength, such that if an intrinsically fluorogenic adenoviral structural protein is in the medium it will emit radiation having an emission wavelength characteristic of an intrinsically fluorogenic adenoviral structural protein. The adenoviral protein content of the medium is evaluated by determining whether radiation having an emission wavelength characteristic of an intrinsically fluorogenic adenoviral structural protein is emitted from the medium.

The medium can be provided by the use of chromatography to separate a composition containing an intrinsically fluorogenic adenoviral structural protein, such that an eluted portion of the composition will contain an adenoviral vector structural protein, if present, as described herein. Moreover, the method can include quantification of the number of adenoviral structural proteins in the medium. The intrinsically fluorogenic adenoviral structural protein can be part of a larger complex, for example, a complex of proteins, or even part of a different type of vector.

Numerous alternative and equivalent techniques and devices to those described herein as useful in the context of the present invention are possible. Several of such techniques and devices are known in the art, and are described in, for example, Brand, L. and Johnson, M. L., Eds., *Fluorescence Spectroscopy* (*Methods in Enzymology, Volume 278*), Academic Press (1997); Cantor and Schimmel, *Biophysical Chemistry*, W. H. Freeman & Co. (New York) (11th Printing 1998), Dewey, T. G., Ed., *Biophysical and Biochemical Aspects of Fluorescence Spectroscopy*, Plenum Publishing (1991); Guilbault, G. G., Ed., *Practical Fluorescence, Second Edition*, Marcel Dekker (1990); Lakowicz, J. R., Ed., *Topics in Fluorescence Spectroscopy: Techniques*, Volumes 1–5 (1991); Plenum Publishing; Lakowicz, J. R., *Principles of Fluorescence Spectroscopy*, Second Edition, Plenum Publishing (1999); and Sharma, A. and Schulman, S. G., *Introduction to Fluorescence Spectroscopy*, John Wiley and Sons (1999).

EXAMPLES

The following examples further illustrate the present invention but should not be construed as in any way limiting its scope.

Example 1

This example demonstrates the identification of excitation and emission wavelengths for the intrinsically fluorogenic portion of a viral vector particle.

A 100 µl solution containing approximately $1.3 \times 10^9$ anion exchange chromatography-purified, wild-type adenovirus particles (serotype 5) was obtained. No fluorescent dyes or fluorophores were in, or added to, the solution. The solution was placed in a Hewlett Packard 1100 scanning Fluorescence Detector, equipped with a xenon flash excitation radiation source and a PMT detector. The solution was scanned to determine whether the adenovirus particles were intrinsically fluorogenic by contacting the solution with UV radiation emitted from the xenon flash lamp at wavelengths between 220 nm and 250 nm. An emission peak was detected when the solution was contacted with excitation radiation having an excitation wavelength at about 235 nm. Thus, it was determined that the adenovirus particles contain a naturally-occurring intrinsically fluorogenic portion.

Emission wavelengths then were scanned by fixing the excitation radiation at 235 nm (+/−10 nm), contacting the solution with the excitation radiation, and detecting whether fluorescent emissions having emission wavelengths of between 300 nm and 600 nm were produced. A prominent emission wavelength was observed at about 330 nm.

Excitation wavelengths were re-scanned by fixing detected emission wavelengths at 330 nm and scanning excitation wavelengths from 200 nm to 300 nm. Two excitation wavelengths, one at about 234 nm and another at about 284 nm, which resulted in significant fluorescent emissions at 330 nm, were observed.

Emission wavelengths were then re-scanned by fixing the excitation wavelength at 281 nm (+/−10 nm) and detecting whether fluorescent emissions having emission wavelengths of between 300 nm and 700 nm were produced. Two emission wavelengths were observed: one at about 330 nm, and, surprisingly, a second emission wavelength at about 574 nm, which is well above emission wavelengths associated with aromatic amino acids (282–348 nm), pyrimidine nucleotide bases (260–275 nm), and purine nucleotide bases (260–267 nm). Fluorescent emissions at the 574 nm emission wavelength were determined to be more selective for the adenovirus particles (i.e., emissions at this wavelength tended to be associated with less background fluorescence and/or undesired excitation of other molecules in the solution) and resulted in significantly higher emission intensity than at 330 nm, indicating that this emission wavelength was the optimum wavelength, and, thus, also capable of providing the most sensitive detection.

The results of these experiments demonstrate how excitation wavelengths and emission wavelengths can be determined for a viral vector particle containing an intrinsically fluorogenic portion, such as an adenoviral vector particle. The results also demonstrate that viral vector particles which are associated with more than one excitation emission wavelength can be detected using the method of the invention, and that such wavelengths can be exploited to provide more sensitive and/or more selective viral vector particle detection. Furthermore, these results demonstrate that viral vector particles having an emission wavelength of between 560–590 nm can be detected by fluorescent detection.

Example 2

This example demonstrates the relationship between emission intensity and total number of adenoviral vector particles in a medium.

A medium containing $3.84 \times 10^9$ unmodified serotype 5 adenovirus particles was subjected to six repeated 1:3 serial dilutions. At each dilution of the medium, three 100 μl samples of the diluted medium were obtained and subjected to excitation radiation at 235 nm and fluorescence detection using a Hewlett Packard 1100 Fluorescence Detector, as described in Example 1. The excitation radiation wavelength was set at 235 nm.

Emission radiation having an emission wavelength of 330 nm and the corresponding intensity of the emission wavelength for each of the samples was detected by a PMT contained in the fluorescence detector. Intensity was measured in relative light units (RLUs). An emission spectrum corresponding to detected emission wavelengths and intensities was produced. The area under each peak in the emission spectrum was integrated by ChemStation 3D version 8.0 (Hewlett Packard). Integrated peak areas for each sample at each dilution were averaged except for results which varied more than 5% from the mean peal area at a given dilution which were not considered. The results of these experiments are presented in Table 2.

TABLE 2

Adenovirus Particle Number and Fluorescence Intensity

| Estimated Number of Adenovirus Particles in the Diluted Medium | Fluorescence Intensity (RLU) |
| --- | --- |
| $5.27 \times 10^6$ | 9.6 |
| $1.58 \times 10^7$ | 26 |
| $4.74 \times 10^7$ | 84 |
| $1.42 \times 10^8$ | 273 |
| $4.27 \times 10^8$ | 876 |
| $1.28 \times 10^9$ | 2525 |

These results were plotted on a graph of the number of adenovirus particles in the diluted medium versus the intensity of the fluorescence intensity. The plotted data formed a line. The linear nature of the relationship between viral vector particle number and fluorescent intensity was confirmed by linear regression analysis. The regression coefficient was determined to be 0.9998.

These results show that mediums containing viral vector particles which include an intrinsically fluorogenic portion exhibit fluorescence intensity in a linear relationship to the number of viral vector particles in the medium, and, thus, are subject to quantification by fluorescent detection. The results further demonstrate that this linear relationship extends across a wide range of total viral vector particle numbers (e.g., from about $5.27 \times 10^6$ particles to about $1.28 \times 10^9$ particles). Thus, the present invention provides a method of quantifying the number of viral vector particles in a medium by fluorescent detection.

Example 3

This example demonstrates numerous aspects of the present inventive method including the increased sensitivity of the inventive method over presently used UV spectrophotometry-based techniques, as well as the relative quantification of intact adenovirus particles and the relative quantification of defective and empty adenovirus particles by fluorescence detection in various mediums.

Cells infected with unmodified serotype 5 adenovirus were harvested to obtain a crude cell lysate using standard techniques. A sample of the crude cell lysate was obtained.

Two additional samples were prepared as follows: Two aliquots of the remaining cell lysate were obtained and subjected to purification by contact with an anion exchange high performance liquid chromatography column (AE-HPLC) as described in International Patent Application WO 99/54441, or by separation on a cesium chloride density gradient repeated three times (i.e., triple, or 3×, CsCl density gradient purification). Volumes equal to the crude lysate sample were obtained for both purified samples.

Yet two more samples were prepared as follows: Another aliquot of the cell lysate was subjected to AE-HPLC purification followed by one time (i.e., 1×) CsCl density gradient purification. After 1×CsCl density gradient purification, two distinct bands on the AE-HPLC column eluant (an upper and lower band), corresponding to the purified AE-HPLC eluant were observable. Samples extracted from each band, in a volume equal to the aforementioned samples, were obtained to provide an upper band sample and a lower band sample. Mass spectrometry analysis determined that the upper band sample contained higher quantities of incompletely processed (i.e., empty and defective) adenovirus particles than the lower band sample, and even more defective and empty particles than the crude cell lysate.

Each of the aforementioned five samples was divided into three equal volumes. The equal volumes were separately injected into an analytical chromatography column which was connected to both a UV spectrophotometer and the fluorescence detector described in Example 1. Thus, the portions of the samples eluted from the analytical column were subjected to UV spectrophotometry-based absorbance analysis as well as excitation and fluorescence detection almost immediately following elution. The time of elution from the analytical column and absorbance of fluorescence detection were determined. Elution times for viruses detected by absorbance and excitation varied by 1 second or less.

Absorbance quantification was performed at 260 nm for each portion eluted from the analytical column using standard techniques. The eluant obtained from the first equal volume of each sample was contacted with excitation radiation having an excitation wavelength (Ex) of 235 nm. This was followed by fluorescence detection at the 330 nm emission wavelength (Em). The eluants obtained from the second and third equal volumes of each sample were contacted with excitation radiation at 284 nm, which was followed by fluorescence detection at either the 330 nm or 574 nm emission wavelength, respectively. Fluorescent intensity in all cases was measured in relative light units.

Absorbance and fluorescence intensities for adenovirus particles in each eluted portion were separately plotted against time of elution to provide two dimensional graphs containing absorbance or emission peaks. Integrated peak areas for absorbance, and for fluorescence intensity corresponding to each of the excitation and emission wavelength combinations used (i.e., 235 nm Ex: 330 nm Em, 284 nm Ex: 330 nm Em, and 284 nm Ex: 574 nm Em), were determined. Normalized values for each portion were determined by dividing the integrated area of the fluorescence peaks by the integrated area of the absorbance peaks. The results of these calculations are shown in Table 3.

TABLE 3

Normalized Fluorescence/Absorbance Values for Adenoviral Vector Particles in Various Mediums

| | Fluorescence Intensity Peak Area (Ex = 235 nm:Em = 330 nm)/Absorbance Peak Area (260 nm) | Fluorescence Intensity Peak Area (Ex = 284 nm:Em = 330 nm)/Absorbance Peak Area (260 nm) | Fluorescence Intensity Peak Area (Ex = 284 nm:Em = 574 nm)/Absorbance Peak Area (260 nm) |
|---|---|---|---|
| Crude cell lysate | 16.0 | 22.3 | 14.4 |
| AE-HPLC purified lysate | 16.0 | 22.3 | 20.5 |
| 3x CsCl density-gradient purified lysate | 14.3 | 20.2 | 19.6 |
| AE-HPLC purified + 1x CsCl density gradient purification (lower band) | 14.2 | 19.5 | 19.1 |
| AE-HPLC purified + 1x CsCl density gradient purification (upper band) | 15.0 | 21.1 | 13.1 |

The results of these experiments are significant in many respects. First, the normalized values in Table 3 are indicative of the relative sensitivity of the inventive method as compared to UV spectrophotometry-based absorbance analysis. Particularly, as can be seen from the data set forth in Table 3, the fluorescence detection methods of the present invention are more sensitive than detection methods based on UV absorbance.

Second, the results of these experiments demonstrate quantification of the number of adenovirus particles in a medium by the inventive method. For example, the lower band sample, which contained only a portion of the eluant obtained from the AE-HPLC purification step, exhibited significantly lower normalized values than crude cell lysate and AE-HPLC purified samples at the 330 nm emission wavelength. These lower normalized values reflect lower fluorescence intensity at the 330 nm emission wavelength emitting from the lower band sample, and, consequently, reflect a smaller number of viral particles in the lower band sample versus the crude cell lysate and AE-HPLC purified samples, as predicted. Thus, these results confirm that the present invention provides a method for relatively quantifying the number of viral vector particles in a medium by fluorescence detection. The consistent normalized values obtained at 330 nm emission wavelengths for the AE-HPLC purified sample and crude cell lysate sample indicate that nearly all of the particles were retained by the AE-HPLC purification technique and corroborate the ability of the inventive method to quantify the number of viral particles in the medium.

Third, these results demonstrate the relative quantification of defective and empty viral vector particles in a medium by fluorescence detection. For example, as seen in Table 3, the crude cell lysate sample exhibited a significantly lower normalized value, and, thus, lower fluorescence intensity, at the 574 nm emission wavelength, than the AE-HPLC purified sample. The upper band sample exhibited an even more significant decrease in normalized value at the 574 nm emission wavelength as compared to the AE-HPLC purified sample. The decrease in fluorescence intensity at the 574 nm emission wavelength observed in the crude cell lysate and upper band samples versus the AE-HPLC purified sample corresponds to the higher number of defective and empty particles in these samples, as confirmed by mass spectrometry experiments. Similarly, the relatively higher fluorescence intensity at the 547 nm emission wavelength observed for the lower band sample versus the AE-HPLC purified sample corresponds to the lower number of defective and empty particles in this sample, as also confirmed by mass spectrometry experiments.

Using fluorescent emissions at the 574 nm emission wavelength from the upper band as a standard signal, and by performing a linear regression analysis, the relative percentage of empty and defective particles in other samples was determined. For example, by performing such an analysis it was determined that the AE-HPLC sample contained about 11.5% of the number of empty and defective particles contained in the upper band sample.

The results of these experiments also confirm that the 330 nm emission wavelength is relative damage-insensitive for adenovirus particles and that the 574 nm emission wavelength is a damage-sensitive emission wavelength for adenovirus particles, which is associated with an intensity shift. The relative consistency of fluorescence intensity at the 330 nm emission wavelength for the various samples confirms that this wavelength is a relatively damage-insensitive wavelength. The relative variance of fluorescence intensity at the 574 nm emission wavelength between the various samples known to differ as to the quantity of damaged viral vector particles confirms that this wavelength is a damage-sensitive wavelength for adenovirus particles. Thus, the normalized value (or fluorescence intensity) observed at the 330 nm emission wavelength can be used to calculate the total number of particles, and the value obtained at the 574 nm emission wavelength can determine what proportion of those particles are damaged.

This experiment demonstrates that the present inventive method can be used to quantify the number of viral vector particles in a medium and/or quantify the number of damaged (e.g., defective and empty) viral vector particles in a medium.

Example 4

This example demonstrates the separation and identification of the intrinsically fluorogenic components of adenovirus particles and the evaluation of the intrinsically fluorogenic adenoviral structural protein content of a medium.

A first solution containing $1.9 \times 10^9$ intact wild-type serotype 5 adenovirus particles and a second solution containing $3.5 \times 10^{10}$ intact wild-type serotype 5 adenovirus particles were obtained using standard techniques. Each solution was subjected to C4 reverse phase chromatography without disassociation of the adenovirus particles prior to contacting the reverse phase column with the solutions. The adenovirus particles were separated into their constituent molecules by contact with the reverse phase chromatography resin, and the separated compounds were eluted from the resin. The time of elution of the components was determined.

After elution, the eluted portion of the second solution was subjected to UV spectrophotometry at 214 nm to identify the separated components of the adenovirus particles. The resulting absorbance was plotted on a graph against the time of elution of the components. Peak area was determined to identify the proportion of the total adenovirus protein content corresponding to each detected component.

Similarly, after elution, the eluted portion of the first solution was subjected to excitation radiation having an excitation wavelength at 235 nm and fluorescent detection for emissions having an emission wavelength at 330 nm using the techniques described in Example 1 to determine which of the identified components were intrinsically fluorescent. Fluorescence intensity was plotted on a graph against the time of elution of the fluorescent components. Peak area was determined to identify the proportion of the fluorescence intensity of each fluorogenic component to the combined fluorescence for all components, thereby enabling determination of the relative fluorescence of the intrinsically fluorogenic components.

Significant absorbance peaks were observed for components eluted from the resin at about 9.5 minutes, 10 minutes, 10.5 minutes, 11.5 minutes, 12 minutes, 12.5 minutes, 14 minutes, 15 minutes, 22 minutes, and 24 minutes. These peaks were correlated with fluorescence peaks observed for components eluted from the resin at about 2.5 minutes, 12 minutes, 13.5 minutes, 15.5 minutes, 16 minutes, 18 minutes, 19 minutes, 26 minutes, and 28 minutes. Other peaks were determined to be caused by defective or empty adenovirus particles or buffers in the solution and were not further analyzed. Correlation of the detected components was confirmed, and molecules identified, by enzymatic digestion and mass spectrometry analysis (including amino acid sequencing) of the eluted components for both solutions.

By comparing the resulting absorbance and fluorescence spectrums, it was determined that the absorbance peak corresponding to the component eluted at 9.5 minutes was not represented by a corresponding peak in the fluorescence spectrum. By mass spectrometry analysis it was determined that this component consists of the N-terminal portion of the adenovirus major core protein (protein VII). In contrast, each of the other detected components were determined to fluoresce when contacted with excitation radiation at 235 nm.

Comparisons were made between the areas of the absorbance peaks and the fluorescence peaks to determine the relative component content of the elution and its proportional contribution to the total fluorescence of the solution. By making such comparisons the fluorescent qualities of the components was relatively determined. For example, the adenovirus protein hexon, which eluted at 22 minutes in solution, was determined by its absorbance peak area to make up 52% of the total protein content of the adenovirus particles (consistent with published figures), whereas its fluorescent emission contribution was about 75% of the total detected fluorescence of the components. Thus, hexon was identified as a strong intrinsically fluorogenic adenoviral protein. Other intrinsically fluorogenic adenovirus structural proteins identified by these experiments include the adenovirus fiber and penton proteins. Similar emission patterns were seen in other experiments performed using excitation radiation having an excitation wavelength of 284 nm and fluorescence detection at 330 nm.

These results demonstrate that components of intrinsically fluorogenic portions of viral vector particles can be separated and evaluated by fluorescence detection. Moreover, these results demonstrate that the adenoviral vector structural protein content of a medium can be determined by fluorescence detection.

All references, including publications, patent applications and patents, cited herein are hereby incorporated by reference to the same extent as if each reference were individually and specifically indicated to be incorporated by reference and were set forth in its entirety herein. The use of the terms "a" and "an" and "the" and similar referents in the context of describing the present invention (especially in the context of the following claims) are to be construed to cover both the singular and the plural, unless otherwise indicated herein or clearly contradicted by context. The use of the terms "including," "having," "comprising," "containing, " and similar terms are to be construed as open-ended terms (i.e., meaning "including, but not limited to") unless otherwise indicated. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illustrate the present invention and is not intended as a limitation on the scope of the claimed invention. No language in the specification should be construed as indicating any non-claimed element as essential to the practice of the invention.

The foregoing is an integrated description of the invention as a whole, not merely of any particular element or facet thereof. The description describes "preferred embodiments" of this invention, including the best mode known to the inventors for carrying it out. Upon reading the foregoing description, variations of those preferred embodiments may become apparent to those of ordinary skill in the art. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is possible unless otherwise indicated herein or otherwise clearly contradicted by context.

What is claimed is:

1. A method of evaluating the content of a particular intrinsically fluorogenic adenoviral structural protein in a composition, the method comprising:

(a) contacting a composition with a chromatography resin, (b) eluting at least a portion of the composition from the chromatography resin such that if the particular intrinsically fluorogenic adenoviral structural protein is in the composition it will elute at a known time and in substantial absence of other intrinsically fluorogenic adenoviral structural proteins, (c) obtaining the portion of the composition which will contain the particular intrinsically fluorogenic adenoviral structural protein, if present in the composition, to provide a medium, (d) contacting the medium with an excitation radiation comprising an excitation wavelength of about 284, such that if the particular intrinsically fluorogenic adenoviral structural protein is in the medium it will emit radiation comprising an emission wavelength of about 330 nm, and (e) evaluating the content of the particular intrinsically fluorogenic adenoviral structural protein in the composition by determining whether radiation comprising an emission wavelength of about 330 nm is emitted from the medium.

2. The method of claim 1, wherein the particular intrinsically fluorogenic adenoviral structural protein is hexon.

3. The method of claim 1, wherein the particular intrinsically fluorogenic adenoviral structural protein is fiber.

4. The method of claim 1, wherein the particular intrinsically fluorogenic adenoviral structural protein is penton base.

5. A method of evaluating the content of a particular intrinsically fluorogenic adenoviral structural protein in a composition, the method comprising:

(a) contacting a composition with a chromatography resin, (b) eluting at least a portion of the composition from the chromatography resin such that if the particular intrinsically fluorogenic adenoviral structural protein is in the composition it will elute at a known time and in substantial absence of other intrinsically fluorogenic adenoviral structural proteins, (c) obtaining the portion of the composition which will contain the particular intrinsically fluorogenic adenoviral structural protein, if present in the composition, to provide a medium, (d) contacting the medium with an excitation radiation comprising an excitation wavelength of about 235, such that if the particular intrinsically fluorogenic adenoviral structural protein is in the medium it will emit radiation comprising an emission wavelength of about 330 nm, and (e) evaluating the content of the particular intrinsically fluorogenic adenoviral structural protein in the composition by determining whether radiation comprising an emission wavelength of about 330 nm is emitted from the medium.

6. The method of claim 5, wherein the particular intrinsically fluorogenic adenoviral structural protein is hexon.

7. The method of claim 5, wherein the particular intrinsically fluorogenic adenoviral structural protein is fiber.

8. The method of claim 5, wherein the particular intrinsically fluorogenic adenoviral structural protein is penton base.

* * * * *